United States Patent [19]

Kremer, Jr. et al.

[11] 4,116,387
[45] Sep. 26, 1978

[54] MIST GENERATOR

[75] Inventors: Carl P. Kremer, Jr., Darien; Mark O. Powers, Norwalk, both of Conn.

[73] Assignee: Eastfield Corporation, Darien, Conn.

[21] Appl. No.: 685,307

[22] Filed: May 11, 1976

[51] Int. Cl.[2] .......................................... A61M 11/02
[52] U.S. Cl. .................................. 239/338; 128/194;
239/366; 239/370; 239/403; 239/427.3;
239/432; 261/78 A
[58] Field of Search ...................... 239/1, 8, 338, 340,
239/366, 367–371, 399, 403, 405, 427, 427.3,
432, 433, 434.5; 128/188, 194; 222/193, 194,
400.7, 405, 424.5; 261/DIG. 65, 78 A

[56] References Cited

U.S. PATENT DOCUMENTS

| 1,594,641 | 8/1926 | Starr | 239/8 |
|---|---|---|---|
| 1,839,193 | 1/1932 | Blanchard | 239/338 X |
| 2,709,577 | 5/1955 | Pohndorf et al. | 239/338 X |
| 2,795,461 | 6/1957 | Durkin | 239/434.5 X |
| 2,840,417 | 6/1958 | Dorsak et al. | 239/338 X |
| 2,869,188 | 1/1959 | Cameto | 239/338 X |
| 3,097,645 | 7/1963 | Lester | 239/338 |
| 3,527,411 | 9/1970 | Colgan | 239/338 |
| 3,630,412 | 12/1971 | Capener et al. | 239/1 |
| 3,745,991 | 7/1973 | Gauthier et al. | 128/194 X |

FOREIGN PATENT DOCUMENTS

| 466,097 | 6/1950 | Canada | 239/427.3 |
|---|---|---|---|
| 548,068 | 9/1956 | Italy | 128/194 |
| 640,808 | 7/1950 | United Kingdom | 239/338 |
| 5,222 of | 1912 | United Kingdom | 239/434.5 |

Primary Examiner—Evon C. Blunk
Assistant Examiner—Andres Kashnikow
Attorney, Agent, or Firm—Eugene E. Geoffrey, Jr.

[57] ABSTRACT

A mist generator for producing mists having fine particle sizes which includes a jet for aspirating a liquid such as water, oil, paints, liquid suspensions and the like, a series of chambers through which said mist is successively passed and deflecting the flow of said mist by baffles, auxiliary gas jets and the like to remove the larger mist particles.

19 Claims, 11 Drawing Figures

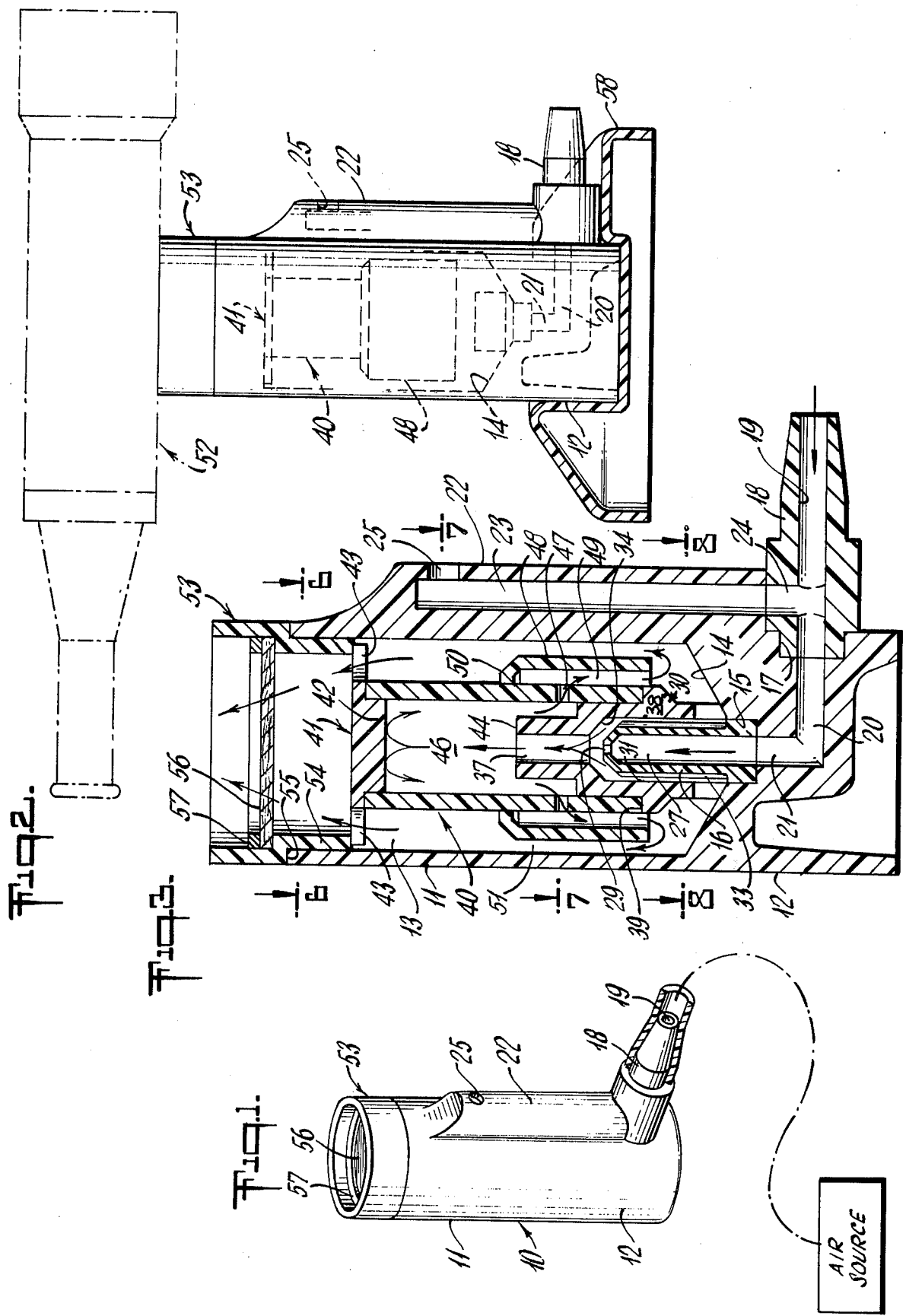

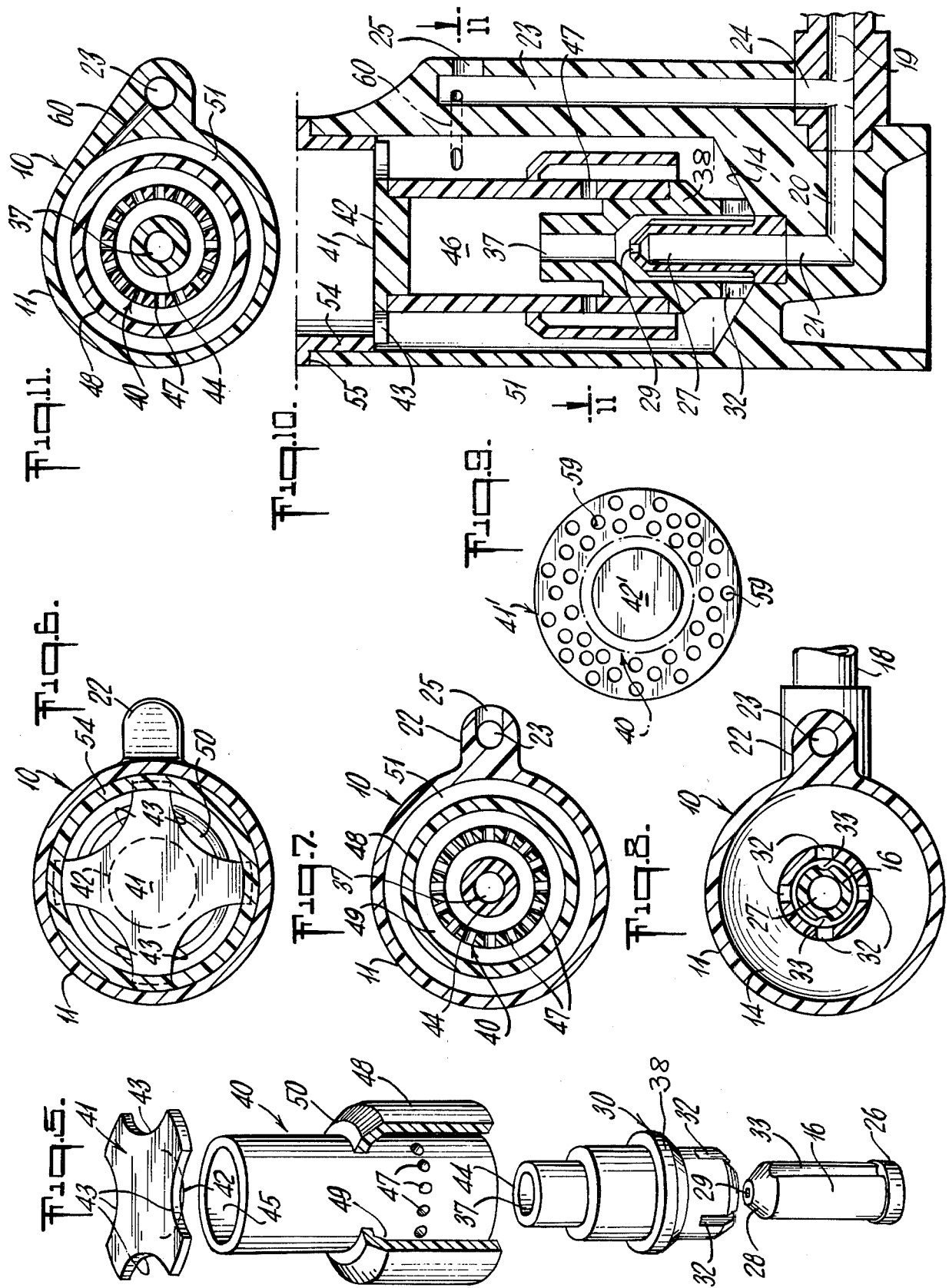

MIST GENERATOR

This invention relates to mist generators and more specifically to a novel and improved method and apparatus for producing mists having exceedingly small particle sizes.

Mist generators, nebulizers and the like have been made for a wide variety of purposes such as therapeutic applications including humidification and the spraying of oils, paints, fertilizers and other liquids. In many applications the particle size is not of particular importance though in many cases such as therapeutic applications and in atomizing oils for heating purposes particle size is extremely important. It has also been found that particle size has a significant effect when treating respiratory diseases.

Known mist generators generally produce mist particles of the order of 1 micron or larger depending upon the sophistication of the apparatus and the air pressures utilized, while others have produced particle sizes as small as 0.5 microns though the mists were not generally uniform and contained particles greater than 0.5 microns.

This invention provides a novel and improved generator that will produce mists having particle sizes of the order of 0.2 microns.

A still further object of the invention resides in the provision of a novel and improved mist generator for producing exceedingly fine mists and may be utilized with air or other gas pressures as low as 5 to 7 pounds per square inch to as high as 90 pounds per square inch.

Another object of the invention resides in the provision of a novel and improved method and apparatus for producing exceedingly fine mists from liquids, such as water, oils, paints and the like as well as liquid suspensions.

Still another object of the invention resides in the provision of a novel and improved mist generator characterized by its simplicity, smoothness of operation and relatively low cost.

The foregoing objects of the invention are obtained through the use of an improved aspirating structure and the treatment of the resultant mist to remove the large particles and only permit discharge of the smaller particles. Air or other compressed gas enters a central opening and emerges in a chamber which is also coupled by appropriate passages to a liquid well. This action draws liquid into the chamber and produces a mist which is then passed through successive chambers to remove the large particles. The invention in other forms involves the utilization of an auxiliary jet and filtering means to enhance the turbulence of the mist and effect the generation of a mist having a substantially uniformly small particle size.

The above and other advantages of the invention will become evident from the following description and accompanying drawing forming part of this application.

In the drawings:

FIG. 1 is an elevational view of one embodiment of a mist generator in accordance with the invention.

FIG. 2 is an enlarged elevational view of the mist generator shown in FIG. 1 with internal portions shown in dotted outline and a discharge nozzle shown in broken lines.

FIG. 3 is an enlarged cross sectional view of the generator shown in FIG. 1.

FIG. 5 is an exploded perspective view of the mist generating elements illustrated in FIG. 3.

Figure 4:
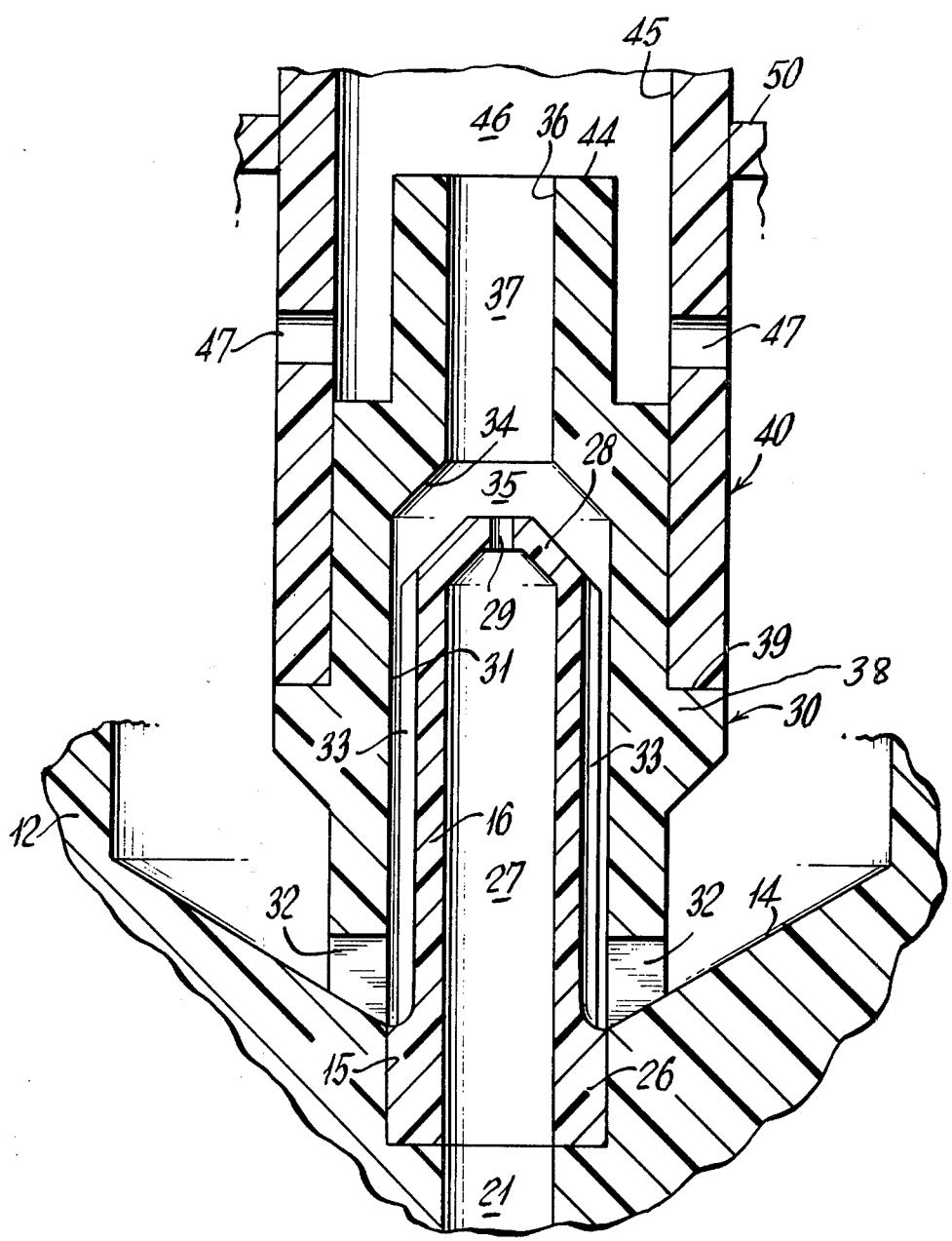
FIG. 4 is a greatly enlarged cross sectional view of a fragmentary portion of FIG. 3.

FIGS. 6, 7, and 8 are cross sectional views taken along the lines 6—6, 7—7, and 8—8 of FIG. 3.

FIG. 9 is a plan view of a modified form of plate overlying the mist generating portions.

FIG. 10 is a cross sectional view of a modified embodiment of the mist generator illustrated in FIGS. 1 through 8, and FIG. 11 is a cross sectional view of FIG. 10 taken along the line 11—11 thereof.

Referring now to the drawings and more specifically to FIGS. 1 through 8, the mist generator in accordance with the invention is generally denoted by the numeral 10 and comprises a cylindrical body 11 having a closed bottom portion 12 and forming a chamber 13 therein. The bottom of the chamber 13 has downwardly and inwardly sloping walls 14 and a central opening 15 formed therein to receive and support the nozzle 16. The base of the body 11 also includes a recess 17 to receive a gas inlet coupling 18 having a passage 19 extending therethrough. This passage is coupled with passages 20 and 21 formed within the base of body 11 and communicating with the central opening 15. The body 11 further includes an elongated structure 22 extending along one side thereof and which may be integrally formed with the housing. The structure includes an elongated passage 23 extending therethrough and communicating with passage 24 formed in the coupling 18 and intersecting the passage 19. A hole 25 is formed in the upper end of the structure 22 and intersects the passage 23. With this arrangement when compressed gas is fed into the passage 19, it will normally exhaust through the passage 23 and opening 25. However, by closing the opening 25 by any suitable means such as the tip of the finger, air will then be forced through the passages 20 and 21 and thence upwardly into the chamber 13 within the housing 11.

Aspiration of a liquid contained in the bottom of the chamber 13 is effected by the nozzle 16 which comprises an elongated tubular structure having an enlarged bottom portion 26 securely retained within the opening 15. The passage 27 within the nozzle 16 is aligned with the passage 21 in the base 12 and the upper end 28 of the nozzle is tapered inwardly and has a relatively small opening 29 therein for discharge of the gas. While this opening may be of any desired diameter, in the illustrated embodiment of the invention it has been found that an opening of the order of 0.03 inches in diameter has been found to be effective. The outer surface of the nozzle tip is provided with a taper which may be of the order of approximately 45°.

A first sleeve generally denoted by the numeral 30 has an enlarged central opening 31 only slightly greater than the outside diameter of the nozzle 16, and it is desirable to maintain the clearance between the wall of the opening 31 and the outside diameter of the nozzle as small as possible. The bottom end of the sleeve 30 is provided with a plurality of slots 32 and the bottom edge is preferably tapered to conform with the slope of the concavity 14 in the bottom of chamber 13. The nozzle 16 has at least two vertically disposed grooves 33 in the surface thereof to facilitate the aspiration of liquid in the bottom of chamber 13 upon the expansion of compressed air from the nozzle opening 29. It has been found that with the use of two grooves in the form of semi-circular channels having a radius of the order of 0.030 inches smooth, uniform operation can be attained.

The opening 31 within the sleeve extends approximately to the top end of the nozzle 16 and the walls taper inwardly as indicated by the numeral 34 at an angle preferably parallel to the taper on the end of the nozzle 16 to form the chamber 35. The upper portion 44 of the sleeve 30 is of reduced diameter and has an opening 36 forming in effect a narrowed chamber 37. The periphery of the sleeve 30 has an enlarged portion 38 forming a shoulder 39 to receive and support a second sleeve 40 slidably engaging the periphery of the sleeve 30. The sleeve 40 extends beyond the top of the sleeve 30 and is closed by a plate 41 having a section 42 of reduced diameter which tightly engages the top of the sleeve 40 to close the end thereof. The plate 41 also has four notches 43 to provide for the flow of the mist out of the housing 11 as will be described. The upper portion 44 of the sleeve 30 is smaller in diameter than the inner wall 45 of the sleeve 40. The sleeve 40 thus forms a third chamber 46 which extends downwardly about the portion 44 of sleeve 30.

The mist formed in the chamber 35 thus passes through the chamber 37 and expands into the chamber 46 producing substantial turbulence. The mist is then discharged from the chamber 46 through a plurality of radial holes 47 formed in the wall of sleeve 40 and preferably at a point below the upper end 44 of the sleeve 30. In the instant embodiment of the invention it has been found that if the sleeve 40 has a one-half inch outside diameter, 18 openings of the order of 0.05 inches in diameter at spaced intervals of 20° produce excellent results. A baffle 48 surrounds the sleeve 40 and is spaced therefrom to form a channel 49. The upper portion of the baffle 48 is curved inwardly as indicated by the numeral 50 and is secured to the wall of the sleeve 40 so that the mist emerging from the holes 47 must pass downwardly and then upwardly through the space 51 formed between the wall of the housing 11 and the outer surface of the baffle 48. The mist then passes through the recesses 43 in the plate 41 and may either be discharged into the atmosphere or into an appropriate nozzle such as the nozzle 52 as illustrated in broken lines in FIG. 2 or other similar structure depending upon the manner in which the mist is to be dispersed.

For convenience in assembly and disassembly of the structure thus far described, sufficient clearance is maintained between the elements such as nozzle 16, sleeves 30 and 40 and the top closure 41. In this way the structure can be taken apart to facilitate cleaning and sterilization if necessary. To hold the elements in the assembled position, a tubular member or adaptor 53 may be provided which has a lower portion 54 of reduced diameter to snuggly fit within the housing 11 and bear against the plate 41 to hold the elements in the assembled position. The upper portion is of slightly larger diameter and forms a shoulder 55 which seats against the upper end of the housing 11.

While the structures thus far described will produce an exceedingly fine mist of 0.2 microns, it may be desirable to include a filter 56 having exceedingly fine openings therein which overlies the opening in the adapter 53. The filter may be held in position by any suitable means as by a resilient ring 57. If desired, a suitable stand 58 as illustrated in FIG. 2 may be provided to support the mist generator in a substantially vertical position. It will be observed, however, that inasmuch as the bottom wall 14 of the housing 11 is concave, substantially all of the fluid which may be contained therein can be aspirated even though the generator is not maintained in a precisely vertical position. This permits the aspiration of even small quantities of liquid. The flow of gas or air as the case may be and the mist formed by aspiration is indicated by the arrows in FIG. 3 and it has been found that by producing turbulence as a result of the chamber configurations and the circuitous path through which the mist travels, the larger particles are caused to return to the body of fluid in the base of the housing 11 and only the exceedingly fine particles will be discharged.

A modified form of the invention illustrated in FIGS. 1 through 8 is shown in FIG. 9 which is a plan view of a modified plate 41 denoted by the numeral 41'. This plate is identical to the plate 41 except for the fact that it is provided with a plurality of holes 59 which contribute to the creation of increased back pressure and consequently added turbulence to effect removal of the large particles.

The embodiment of the invention illustrated in FIGS. 10 and 11 is identical to the embodiment illustrated in FIGS. 1 through 8 with the exception of an auxiliary air jet and accordingly like numerals have been utilized to denote like components in the two embodiments. Referring more specifically to FIGS. 10 and 11, it will be observed that a passage 60 is formed between the upper part of the passage 23 and the interior of the housing 11 and is substantially tangential to the inner surface of the housing 11. In this way a jet of compressed gas is introduced into housing 11 which imparts circular motion to the mist with the result that the larger particles of greater mass are forced to impinge against the wall of the housing 11 while the smaller and much lighter particles having much less momentum will tend to rise and be discharged. The utilization of this tangential jet of gas further insures the production of a uniform mist. While not illustrated in this embodiment of the invention, a filter 56 as shown for instance in FIG. 3 may be utilized with the form of the invention illustrated in FIGS. 10 and 11.

The embodiments of the invention shown in FIGS. 3, 4 and 10 are approximately to scale and the outside diameter of sleeve 40 is approximately one half inch. The size of the generator may, however, be varied depending on the specific application.

It has been found in actual tests that excellent results were obtained when the nozzle taper was approximately at 45° to the axis of the nozzle opening 29 and wherein the length of the chamber 37 was generally of the order of five times the length of the chamber 35. It is also desirable to position the openings 47 in the sleeve 40 substantially below the top of the chamber 37.

While certain embodiments of the invention have been illustrated and described, it is understood that alterations, changes and modifications may be made without departing from the true scope and spirit thereof.

What is claimed is:

1. A mist generator comprising a housing having a base and a peripheral wall structure extending therefrom, means for aspirating a liquid within said housing to form a mist, said means including a nozzle having an outlet for the discharge of gas under pressure and means communicating with a liquid source for the aspiration thereof in response to gas discharged from said nozzle, a first sleeve in said housing and surrounding said nozzle to form a first chamber adjoining the outlet, a cylindrical member extending from said first sleeve to form a second chamber of smaller area than the first chamber, said mist flowing successively from the first chamber to the second chamber, and second sleeve means communicating with said cylindrical member and including a third chamber for confining said mist and including openings for discharging it into said housing in a direction angularly disposed relative to the direction of emergence of gas from the nozzle, said mist then being discharged from said housing said nozzle extending from said base and terminating in a frustoconical end portion, said first sleeve surrounds said nozzle and forms said communication means for aspiration of liquid into the first chamber, the end of said first sleeve extending at least to the end of the nozzle and having an inwardly formed taper terminating beyond the end of the nozzle in an opening smaller than the cross sectional area of said nozzle and said cylindrical member extends from the first sleeve and has an opening corresponding in cross sectional area to the cross sectional area of the terminal opening of said first sleeve, and said openings for discharging the mist from said third chamber being disposed below the end of said second chamber, said generator further including a baffle surrounding at least a portion of said second sleeve and spaced therefrom, the lower end of said baffle extending below the last said openings to form a circuitous path for the flow of said mist from said third chamber to said housing.

2. A mist generator according to claim 1 including a perforated plate intercepting the mist discharged from said housing.

3. A mist generator according to claim 1 including means for filtering the mist discharged from said housing.

4. A mist generator comprising a housing having a base and a peripheral wall structure extending therefrom, a nozzle centrally disposed within and extending from the base of said housing and having an opening extending therethrough, means for feeding compressed gas upwardly through said nozzle opening, a sleeve surrounding said nozzle, said housing adapted to retain a liquid about the base of the sleeve, said sleeve extending beyond the upper end of said nozzle and terminating in a section having an internal diameter smaller than the internal diameter of the remainder of the sleeve and thereby forming a first chamber adjoining the end of the nozzle and a second chamber communicating with the first chamber, conduit means to facilitate the flow of said liquid into said first chamber in response to the flow of gas through said nozzle, means including a closed chamber coupled to and extending below the second chamber and having radial openings at the base portion thereof and below the outer end of said second chamber and a baffle at least partially surrounding the last said chamber in spaced relationship thereto and overlying the openings therein for modifying the direction of flow of said mist from said second chamber into said housing and means on said housing for discharging said mist.

5. A mist generator according to claim 4 wherein said first chamber has conically convergent walls.

6. A mist generator according to claim 5 wherein said second chamber has a length of the order of five times the length of the first said chamber.

7. A mist generator according to claim 5 wherein said conically convergent walls are parallel and at an angle of approximately 45° with the direction of said gas emerging from said nozzle.

8. A mist generator according to claim 7 including means for directing a jet of gas into said housing to impart circular motion to the mist formed therein.

9. A mist generator according to claim 7 wherein said nozzle opening is of the order of 0.03 inches in diameter.

10. A mist generator according to claim 4 wherein said radial openings are of the order of 0.050 inches in diameter.

11. A mist generator according to claim 4 including a compressed gas jet carried by said housing wall for injecting a stream of gas into said housing to impart circular motion to the mist discharged from between said baffle and said closed chamber prior to discharge of the mist from the housing.

12. A mist generator according to claim 4 wherein the inner surface of said base is concave.

13. A mist generator according to claim 4 wherein said second chamber is approximately five times the length of said first chamber.

14. A mist generator according to claim 4 wherein said nozzle opening is approximately 0.03 inches in diameter.

15. A mist generator comprising means for producing a mist, means defining a closed chamber, the first said means extending into said chamber for discharging said mist at a point within said chamber, said chamber defining means having a plurality of openings disposed rearwardly of the point of discharge of said mist into said chamber, a baffle surrounding said chamber defining means and overlying said openings to form a circuitous path for the flow of said mist and a housing surrounding said chamber defining means and including an outlet for discharging said mist.

16. A mist generator according to claim 15 including means for feeding a jet of gas into said housing to impart circular motion to said mist and cause the larger particles through the centrifugal force imparted thereto to strike the wall means defining said housing.

17. A mist generator according to claim 15 wherein said means for producing said mist comprises a tubular nozzle having a frustoconical tip wherein the angle of said cone is at approximately 45° with the axis of said nozzle and a sleeve surrounding said nozzle and defining channel means therebetween, said sleeve extending beyond the end of said nozzle to form a chamber having a maximum diameter at least equal to the outside diameter of said nozzle and a frustoconical inner wall configuration parallel to the tip of said nozzle and spaced therefrom a distance greater than the transverse depth of said channel means, said chamber terminating in an opening spaced forwardly of said nozzle and means for feeding a liquid to be aspirated to said channel means.

18. A mist generator comprising means for producing a mist, means defining a closed chamber, the first said means extending into said chamber for discharging said mist at a point within said chamber, said chamber defining means having a plurality of openings disposed rearwardly of the point of discharge of said mist into said chamber, a housing surrounding said chamber and having an outlet for discharging said mist and means for feeding a jet of gas into said housing to impart circular motion to said mist and cause the larger particles through the centrifugal force imparted thereto to strike said housing.

19. A mist generator according to claim 18 wherein said mist producing means comprises a tubular nozzle having a frustoconical tip wherein the angle of said cone is at approximately 45° with the axis of said nozzle and a sleeve surrounding said nozzle and defining channel means therebetween, said sleeve extending beyond the end of said nozzle to form a chamber having a maximum diameter at least equal to the outside diameter of said nozzle and a frustoconical inner wall configuration parallel to the tip of said nozzle and spaced therefrom a distance greater than the transverse depth of said channel means, said chamber terminating in an opening spaced forwardly of said nozzle and means for feeding a liquid to be aspirated to said channel means.

* * * * *